June 9, 1953 F. MEILLAND Plant Pat. 1,192
ROSE PLANT
Filed June 11, 1952
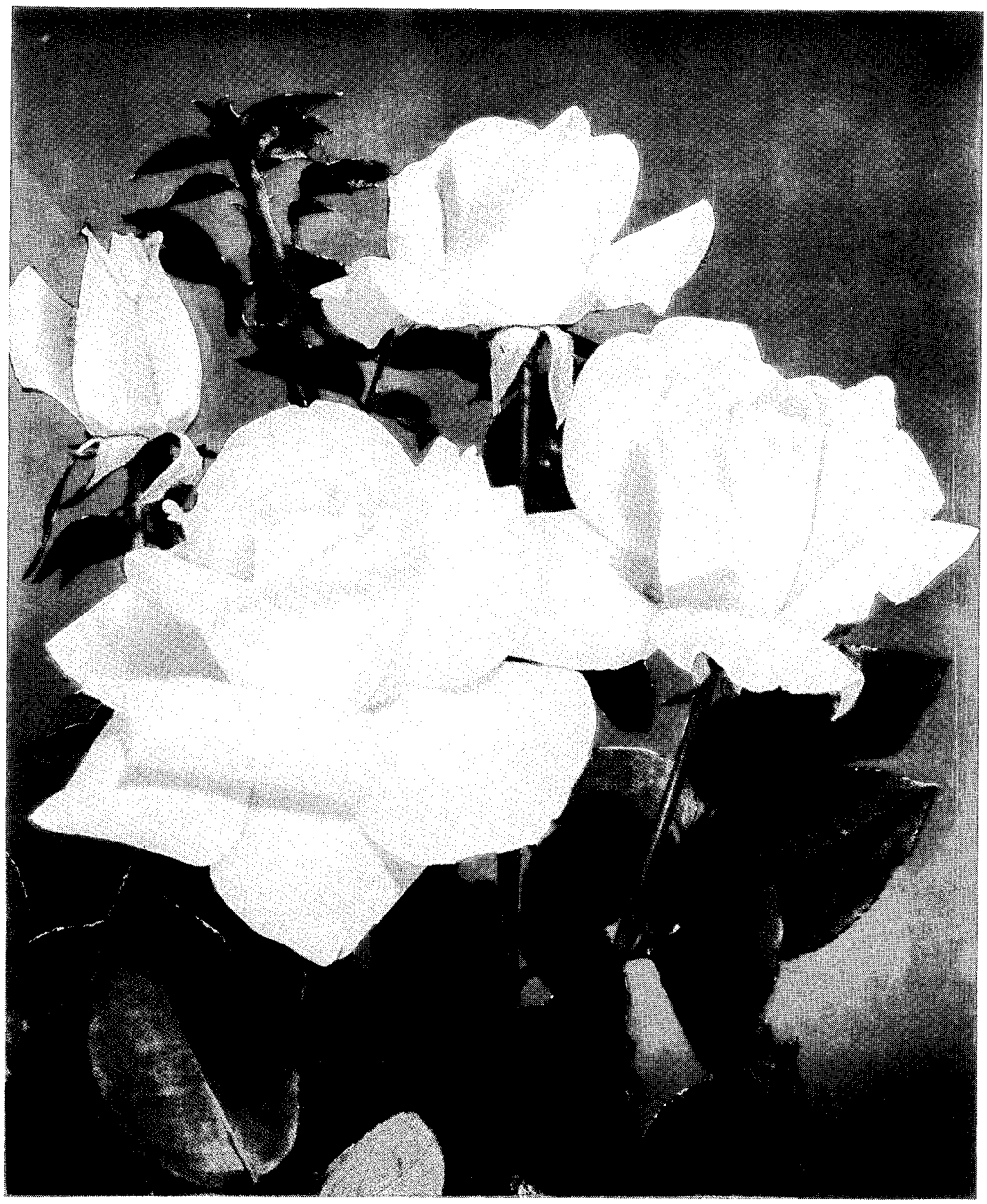
Inventor.
Francis Meilland
By: Robb & Robb.
Attorneys.

Patented June 9, 1953

Plant Pat. 1,192

UNITED STATES PATENT OFFICE 1,192

ROSE PLANT

Francis Meilland, Cap Azura, Cap d'Antibes, France, assignor to The Conard-Pyle Company, West Grove, Pa., a corporation of Pennsylvania Application June 11, 1952, Serial No. 293,031
In France September 24, 1951

1 Claim. (Cl. 47—61)

The present invention relates to a new and distinct variety of rose plant of the hybrid tea class, originated by me by crossing the variety "Peace," known as "Mme. A. Meilland" in France (Plant Patent No. 591), with the variety "Michele Meilland" (unpatented).

The primary objective in making this cross was to produce a new variety of rose of new color and of improved form of bud and bloom. This objective was achieved fully, as evidenced by the unusual coloring and the pearly delicacy of the light, intricately blended colors of the flowers of my new variety as hereinafter more particularly described, in combination with a greater length of its pointed buds and the way the long-pointed, closed center of the flowers is retained through successive stages of the opening bloom while the outer petals develop a symmetrically circular outline around that center, thereby giving the buds and open blooms a grandeur which, in combination with their coloring, distinguishes this new variety from its parents, as well as from all other varieties of its class.

The aforementioned characteristics, together with the sound plant qualities of this new variety, as hereinafter indicated in more particular detail, combine to qualify it as an ideal exhibition type rose.

Asexual reproduction of my new variety by buddings both at Tassin-les-Lyon, France, and at West Grove, Pennsylvania, U. S. A., show that the foregoing characteristics come true to form and are established and transmitted through succeeding propagations.

The accompanying drawing shows specimens of my new variety, with the flowers and foliage in different stages of development, and with the colors depicted in the drawing as nearly true as it is reasonably possible to make the same in an illustration of this character.

The following is a detailed description of my new variety, with color terminology in accordance with Ridgway's Color Standards and Nomenclature, except where general color terminology of ordinary dictionary significance is obvious:

Type: Hardy; bush; outdoor; seedling; for cut flowers and for garden decoration.
Class: Hybrid tea.
Breeding: Seedling.
*Seed parent.*—"Peace."

*Pollen parent.*—"Michele Meilland."
Propagation: Holds its distinguishing characteristics through succeeding propagations by budding.

*Flower*

Locality where grown and observed: West Grove, Pennsylvania, U. S. A.
Flowers borne: Singly to stem; on normal strength, medium length stems.
Quantity of bloom: Free, outdoors.
Continuity: Continuous.
Fragrance: Moderate; tea.
Bud:
*Peduncle.*—Medium length; medium heavy; erect; stiff; moderately rough; medium number of reddish prickles. Color—Dark Olive-Buff, Plate XL, tinged with Pompeian Red, Plate XIII.
*Before calyx breaks.* — Size — medium. Form—medium length; ovoid; with foliaceous appendages on the surface of the bud; with little cut foliaceous parts extending beyond the tip of the bud equal to one-fourth or more of its length.
*As calyx breaks.*—Color—Chalcedony Yellow, Plate XVII, tinged with Geranium Pink, Plate I.
*As first petal opens.*—Size—large. Form—long; pointed; ovoid. Color: outside—Picric Yellow, Plate IV, at base; Barium Yellow, Plate XVI, shaded with Geranium Pink, Plate I, over most of petal surface; inside—Pale Lemon Yellow, Plate IV, at base; light and normal Strawberry Pink, Plate I, over most of petal surface.
*Opening.*—Opens up well.
Bloom:
*Size, when fully open.*—Large; 4½ inches to 5¾ inches.
*Petalage.*—Double; from 28 to 38 petals; arranged regularly.
*Form.*—High centered at first, with petals tightly cupped inward; remaining high centered as outer petals become loosely rolled outward; later at maturity, all petals loosely rolled outward.
Petals: Thick; with inside satiny and outside shiny.
*Shape.* — Outer — obovate. Intermediate — obovate. Inner—obovate.

This description of a newly opened flower was made from a rose grown outdoors in the month of October at West Grove, Pennsylvania, U. S. A.:

*Color.*—Outer petal: outside surface—Martius Yellow, Plate IV, at base, shading to white and Cameo Pink, Plate XXVI, at edges; inside surface—Picric Yellow, Plate IV, at base, shading almost to white and to Cameo Pink, Plate XXVI. Intermediate petal: outside surface—Pinard Yellow, Plate IV, at base, shading to white and then to Safrano Pink, Plate II, at edges; sometimes with tinges of Thulite Pink, Plate XXVI; inside surface—Lemon Yellow, Plate IV, at base, shading to light Orange-Pink, Plate II, and Orange-Pink, Plate II. Inner petal: outside surface—Pinard Yellow, Plate IV, at base, shading to light Baryta Yellow, Plate IV, and to Pale Flesh Color, Plate XIV, at petal edges; inside surface—Lemon Yellow, Plate IV, at base, shading to Seashell Pink, Plate XIV, and shading to Orange-Pink, Plate II, at petal edges.

This description was made from a rose that was open for three days outdoors in the month of October at West Grove, Pennsylvania, U. S. A.:

*Color.*—Outer petal: outside surface—Pinard Yellow, Plate IV, at base, shading to white and/or light Cameo Pink, Plate XXVI; sometimes with tinges of Rosolane Pink, Plate XXVI; inside surface—Picric Yellow, Plate IV, shading almost to white and to Cameo Pink, Plate XXVI, over most of petal surface. Inner petal: outside surface—Martius Yellow, Plate IV, at base, shading to light Ivory Yellow, Plate XXX, and light Marguerite Yellow, Plate XXX; inside surface—Pale Lemon Yellow, Plate IV, at base, shading to Pale Yellow-Orange, Plate III, and Flesh Color, Plate XIV, and almost to white with shadings of Cameo Pink, Plate XXVI.

*General color effect.*—Newly opened flower—Thulite Pink, Plate XXVI, to Cameo Pink, Plate XXVI, at outer edges, shading to Safrano Pink, Plate II, and deep Safrano Pink, Plate II, in center. Three days open—light Cameo Pink, Plate XXVI, at outer edges, shading almost to white and/or with shadings of Pale Flesh Color, Plate XIV, and Pale Orange-Yellow, Plate III, near and at center.

*Behavior.*—Drop off cleanly.

*Flower longevity.*—Cut roses grown outdoors kept at living-room temperature—3 to 4 days in October.

*Reproductive organs*

Stamens: Medium number to many; arranged regularly about pistils.

Filaments: Most with anthers; various lengths from short to medium. Color—Empire Yellow, Plate IV.

Anthers: All open at once; medium size; occasionally an anther fused with a petaloid or pistil. Color—Light Cadmium, Plate IV.

Pollen: Moderate. Color—Light Cadmium, Plate IV.

Pistils: Medium number.

Styles: Uneven; medium length; medium weight; bunched.

Stigma: Color—yellowish white.

Ovaries: Some protruding from calyx.

Sepals: Permanent; medium to long; spear-shaped.

*Plant*

Foliage:

*Leaves.*—Compounds of 3, 5 or 7 leaflets; abundant; medium size; leathery.

*Leaflets.*—Shape—ovoid, with apex acute. Base—obtuse. Margin—simply serrate.

*Color.*—Mature: upper surface—Dark Dull Yellow-Green, Plate XXXII; under surface—Deep Grape Green, Plate XLI. Young: upper surface—Haematite Red, Plate XXVI; under surface—Dark Vinaceous, Plate XXVII.

*Rachis.*—Medium weight. Upper side—grooved. Under side—moderately thorny; sparsely prickly.

*Stipules.*—Medium length; medium width; with medium length points turning out at an angle of less than 90°.

*Disease.*—Resistant to mildew and blackspot, as determined by comparison with other varieties grown under comparable conditions.

Growth:

*Habit.*—Bushy; upright; much branched.

*Growth.*—Free to vigorous.

*Canes.*—Medium heavy.

*Main stems.*—Color—Light Cress Green, Plate XXXI. Thorns—several; medium length; straight; with medium length oval base. Prickles — several; color — Rood's Brown, Plate XXVIII. Hairs—none.

*Branches.*—Color—Dark Citrine, Plate IV. Thorns—few to several; long; straight to pointed downward; with medium length oval base. Prickles—few; color—Pompeian Red, Plate XIII. Hairs—none.

*New shoots.*—Color—Deep Grape Green, Plate XLI, tinged with Pompeian Red, Plate XIII. Thorns—several; medium length; occasionally hooked but usually pointed downward; with medium length oval base. Prickles—none. Hairs—none.

I claim:

A new and distinct variety of rose plant of the hybrid tea class, substantially as herein shown and described, characterized particularly as to novelty by the length of its pointed buds and by the habit of development of the flowers with a long-pointed, closed center which is retained through successive stages of the opening bloom while the outer petals develop a symmetrically circular outline around that center, by the unique coloring of its flowers, by the unusual, pearly delicacy of their light and intricately blended colors, in combination with its sound plant qualities, altogether making the variety an ideal exhibition rose.

FRANCIS MEILLAND.

No references cited.